United States Patent
Oliva

(10) Patent No.: US 8,302,601 B2
(45) Date of Patent: Nov. 6, 2012

(54) INHALER FOR PREPARATIONS IN POWDER FORM

(76) Inventor: Roberto Oliva, Carpi (IT)

( * ) Notice: Subject to any disclaimer, the term of this patent is extended or adjusted under 35 U.S.C. 154(b) by 1104 days.

(21) Appl. No.: 10/594,565

(22) PCT Filed: Mar. 15, 2005

(86) PCT No.: PCT/EP2005/051181
§ 371 (c)(1),
(2), (4) Date: Apr. 17, 2007

(87) PCT Pub. No.: WO2005/089843
PCT Pub. Date: Sep. 29, 2005

(65) Prior Publication Data
US 2007/0277821 A1    Dec. 6, 2007

(30) Foreign Application Priority Data
Mar. 18, 2004 (IT) .............................. MO2004A0060

(51) Int. Cl.
B05D 7/14 (2006.01)
A61M 16/10 (2006.01)

(52) U.S. Cl. .............................. 128/203.15; 128/203.12

(58) Field of Classification Search ............. 128/203.12, 128/203.15, 203.19, 203.21, 200.14–200.23; 222/636, 424.5, 425, 441, 454, 456
See application file for complete search history.

(56) References Cited

U.S. PATENT DOCUMENTS

| | | | | |
|---|---|---|---|---|
| 3,732,864 A | * | 5/1973 | Thompson et al. | 128/200.23 |
| 4,570,630 A | | 2/1986 | Elliott et al. | |
| 5,239,992 A | | 8/1993 | Bougamont et al. | |
| 5,239,993 A | | 8/1993 | Evans et al. | |
| 5,396,883 A | * | 3/1995 | Knupp et al. | 128/200.14 |
| 5,699,789 A | | 12/1997 | Hendricks et al. | |
| 6,065,472 A | * | 5/2000 | Anderson et al. | 128/203.21 |
| 6,382,461 B1 | * | 5/2002 | Olsson | 222/1 |
| 6,481,438 B1 | * | 11/2002 | Gallem et al. | 128/205.23 |
| 6,983,748 B2 | * | 1/2006 | Brown et al. | 128/203.15 |
| 7,207,330 B1 | * | 4/2007 | Braithwaite | 128/203.15 |
| 2002/0033176 A1 | | 3/2002 | Casper et al. | |
| 2002/0033177 A1 | | 3/2002 | Ohki et al. | |
| 2003/0116157 A1 | * | 6/2003 | Braithwaite et al. | 128/203.15 |
| 2003/0164169 A1 | * | 9/2003 | Stangl et al. | 128/203.12 |

FOREIGN PATENT DOCUMENTS

WO    WO 2004/035121 A1    4/2004

* cited by examiner

Primary Examiner — Justine Yu
Assistant Examiner — Rachel Young
(74) Attorney, Agent, or Firm — Browdy and Neimark, P.L.L.C.

(57) ABSTRACT

An inhaler for preparations in powder form, includes a first body (2), which is provided with an inhaling channel (3), and a second body (4), which is provided with at least one reservoir (6), which is open toward the outside and is preset to contain at least one dose of preparation in powder form. The first body (2) is associated with the second body (4) and can move with respect to the second body (4) between a first position, at which it closes the reservoir (6), and a second position, at which at least one connection is open between the reservoir (6) and the inhaling channel (3), making the dose of preparation in powder form available for inhaling.

9 Claims, 2 Drawing Sheets

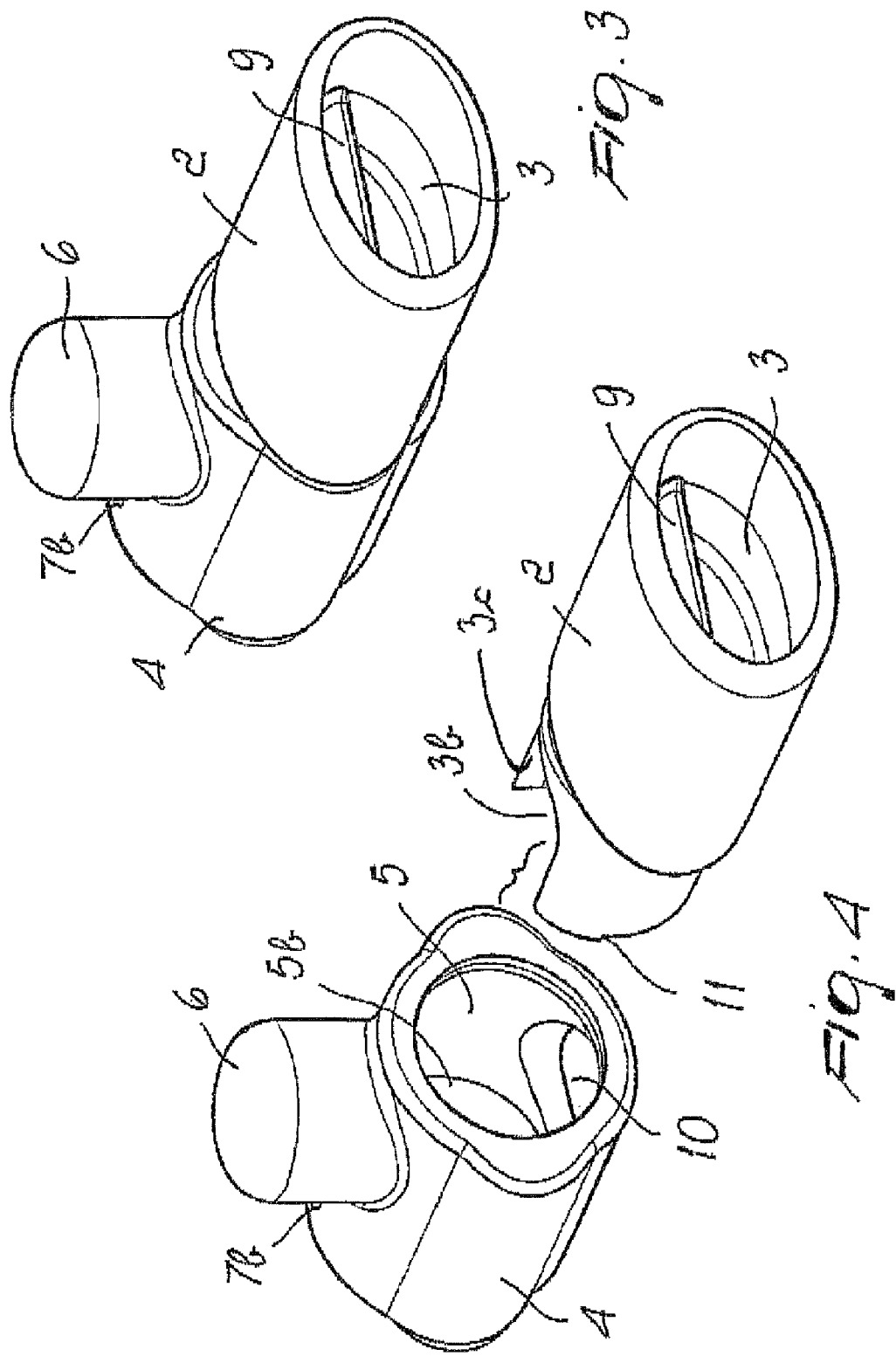

007# INHALER FOR PREPARATIONS IN POWDER FORM

TECHNICAL FIELD

The present invention relates to an inhaler for preparations in powder form. Preferably, the present inhaler is a single-dose inhaler.

BACKGROUND ART

Single-dose inhalers for preparations in powder form are known which use capsules, each of which contains a dose of preparation. The capsules are inserted individually in an inhaler, which in different manners allows to break up the capsule and make the dose of preparation in powder form available for inhaling.

Inhalers of this type are known which are constituted by a container that comprises an inhaling duct, which is connected to a chamber for accommodating a capsule that encloses a drug to be inhaled. Means for breaking the capsule are associated with the containment chamber, are arranged respectively at the ends of the containment chamber and are substantially constituted by two piercing elements, provided respectively with contrast springs and with a certain number of prongs, which can penetrate, by applying pressure thereto with the fingers, into said containment chamber. At this point, the powder can exit from the capsule and be inhaled.

Inhalers of this type have several drawbacks. First of all, they are composed of a relatively large number of components, in view of the presence of the piercing prongs, of the springs and of the ends needed to operate the piercing elements. Some of these components perform a relative motion with respect to the container, and therefore malfunctions or jammings are possible. Moreover, these components require accurate assembly operations in order to be able to operate correctly, and these operations entail an increase in the costs of the inhaler, causing single-use application of the inhaler to be inadvisable.

An improvement to described inhalers has been proposed in a patent application filed by this same Applicant. The inhaler disclosed in said patent application is provided with a main body, which has an inhaling channel to which a secondary body is rotationally coupled, said secondary body comprising a receptacle in which the capsules that contain the preparation in powder form are inserted individually. The secondary body can rotate between an open position, in which the receptacle can be accessed from outside in order to insert the capsules, and a closed position, in which the receptacle is connected to the inhaling channel. The inhaler is also provided with cutting means, which are suitable to cut a portion that protrudes from the receptacle of the capsule during the rotation of the secondary body from the open position to the closed position, so that the contents of the capsule pour into the inhaling duct.

An inhaler of this type, while being cheaper, more functional and reliable than inhalers of other kinds, owing to its configuration, is not intended for single-use application, since it does not comprise a receptacle or reservoir that is suitable to contain a dose of preparation as loose powder, i.e., not enclosed in a capsule, to be released at the time of use.

DISCLOSURE OF THE INVENTION

The aim of the present invention is to provide an inhaler for preparations in powder form that overcomes the limitations of the background art, particularly one which includes the functions of a capsule, in order to contain a dose of preparation in powder form until it is inhaled, and of an inhaler, so as to allow inhalation of the dose of preparation in powder form that it contains.

One advantage of the proposed inhaler is that it is extremely simple, cheap and reliable.

Another advantage of the inhaler is that it is conveniently suitable for single-use application, since it is extremely easy to insert and close a dose of preparation in powder form inside the inhaler and to release said dose for inhaling.

BRIEF DESCRIPTION OF THE DRAWINGS

Further characteristics and advantages of the invention will become better apparent from the following detailed description of an inhaler for preparations in powder form, given hereinafter with reference to the accompanying drawings, provided by way of non-limiting example, wherein:

FIG. 3 is a perspective view of the inhaler of FIGS. 1 and 2;

FIG. 4 is an exploded view of the inhaler of FIG. 3.

WAYS OF CARRYING OUT THE INVENTION

Figure 1:
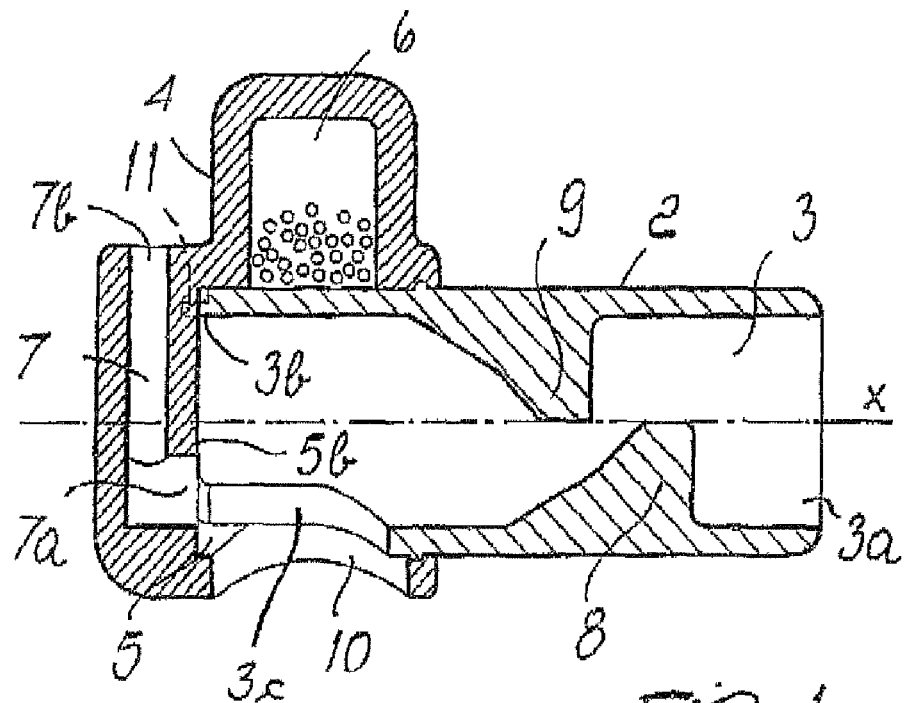
FIGS. 1 and 2 are two sectional views of an inhaler according to the present invention, arranged in two different operating configurations.
Figure 2:
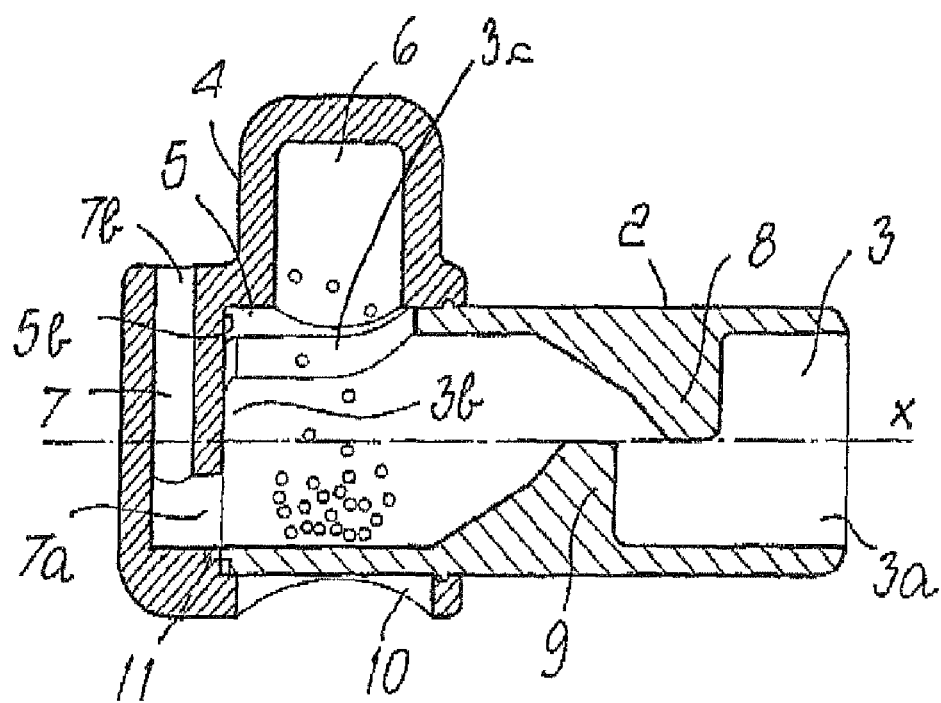

With reference to the figures, which illustrate a preferred embodiment of the invention, an inhaler for preparations in powder form according to the present invention comprises a first body 2, which is provided with an inhaling channel 3, and a second body 4, which is provided with at least one reservoir 6, which is open outward and is preset to contain a dose of preparation in powder form. The first body 2 is associated with the second body 4 and can move with respect to the second body 4 between a first position, at which it closes the reservoir 6, and a second position, at which at least one connection is open between the reservoir 6 and the inhaling channel 3, making the dose of preparation in powder form available for inhaling.

In a preferred embodiment, shown in the accompanying figures, the first body 2 has a longitudinal axis x, about which it preferably has an axially symmetrical shape. At least one portion of the first body 2 is furthermore preferably cylindrical.

The first body 2 is provided longitudinally with a through inhaling channel 3. The inhaling channel 3 is provided with at least one lateral outlet 3c, the longitudinal extension of which is perpendicular to the longitudinal axis x of the first body 2, and has, at its ends, a first outlet 3a and a second outlet 3b, which are arranged approximately at right angles to the longitudinal axis x of the first body 2. The inhaling channel 3 preferably also is axially symmetrical about the longitudinal axis x of the first body 2, so that the first body 2 substantially assumes the shape of a tubular element through the side wall of which, in the portion where the first body 2 is cylindrical, the lateral outlet 3c is provided. In a preferred embodiment, the lateral outlet 3c and the second outlet 3b of the inhaling channel 3 form a single opening, which lies between the end at which the second outlet 3b is arranged and the portion of the lateral surface of the first body 2 on which the lateral outlet 3c is provided.

The second body 4 is provided with a receptacle 5, in which the first body 2 is inserted at least for the part of its longitudinal extension on which the lateral outlet 3c is provided. Preferably, the receptacle 5 is cylindrical and is shaped complimentarily with respect to the cylindrical portion of the first body 2. The end of the first body 2 at which the second outlet 3b of the inhaling channel 3 is arranged is in contact with an end wall 5b of the receptacle 5, which is perpendicular to the longitudinal axis x.

The second body 4 is provided with the reservoir 6, which is preset for containing a dose of preparation in powder form. The reservoir 6 is open toward the receptacle 5 and is shaped like a cylindrical chamber, the longitudinal axis of which is perpendicular to the longitudinal axis x of the first body 2 and the opening of which is provided in a lateral wall of the receptacle 5. In a constructive solution that is not shown and is suitable for multi-dose use of the inhaler, the second body 4 can be provided with a plurality of reservoirs 6, which are mutually separated by a specific angular pitch, each reservoir being open toward the receptacle 5.

The first body 2 can rotate about its own longitudinal axis x with respect to the second body 4 between a first position, at which the lateral outlet 3c of the inhaling channel 3 does not face the opening of the reservoir 6 and the reservoir 6 is not connected to the inhaling channel 3, and a second position, at which the lateral outlet 3c of the inhaling channel 3 faces the opening of the reservoir 6 and the reservoir 6 is connected to the inhaling channel 3. When the first body 2 is turned into the second position, the preparation in powder form contained in the reservoir 6 flows into the inhaling channel 3, passing through the lateral outlet 3c, which faces the opening of the reservoir 6. The two end positions of the rotation of the first body 2 with respect to the second body 4 are formed by way of retention surfaces 11 of a known type, which are only partially visible in the accompanying figures. The retention surfaces 11 are associated with the outer surface of the first body 2 and with the internal surface of the receptacle 5, and are constituted by the end surfaces of two circular arcs that span a right angle and are concentric with respect to the longitudinal axis x of the first body 2. The retention surfaces 11 are preset to mutually abut in pairs at the two end positions of the rotation of the first body 2 with respect to the second body 4. In the multiple-dose embodiment, the second body 4 can rotate between a larger number of positions at which it opens in succession the connections between the reservoirs 6 and the inhaling channel 3.

The second body 4 is provided with a through channel 7, which has a first outlet 7a, which is arranged at the end wall 5b of the receptacle 5, and a second outlet 7b, which is arranged on the outer surface of the second body 4. The first outlet 7a of the through channel 7 is arranged in a position in which it faces the second outlet 3b of the inhaling channel 3, at least at the second position of the first body 2. At least in said second position of the first body 2, the through channel 7 and the inhaling channel 3 form together a single duct. The through channel 7 is substantially the "air intake" of the inhaler: the user aspirates the preparation from the first outlet 3a of the inhaling channel 3, drawing air from outside through the second outlet 7b of the through channel 7. The preparation in powder form, by falling from the reservoir 6 into the inhaling channel 3 through the lateral outlet 3b, lies therefore in an intermediate point of the duct formed together by the inhaling channel 3 and by the through channel 7 and is therefore fully struck by the stream of air generated by the suction produced by the user.

The inhaling channel 3 has at least one first protrusion 8, which protrudes transversely with respect to the longitudinal axis x of the first body 2 from the lateral surface of the inhaling channel 3 toward the inside of the inhaling channel 3. Further, the inhaling channel 3 has at least one second protrusion 9, which protrudes transversely to the longitudinal axis x of the first body 2 from the lateral surface of the inhaling channel 3 toward the inside of the inhaling channel 3.

The second protrusion 9 is spaced with respect to the first protrusion 8 toward the longitudinal axis x of the first body 2 and is arranged opposite, relative to the first protrusion 8, with respect to a central plane of the inhaling channel 3. The protrusions 8, 9 form two obstacles for the stream of air along the inhaling channel 3 produced by the suction performed by the user. The particles of preparation in powder form entrained by the air stream are forced to strike the protrusions 8, 9, disaggregating and breaking up from any larger agglomerations.

In order to avoid stagnation of particles, the protrusions 8, 9 have at least one surface that is inclined and blended with the lateral surface of the inhaling channel 3. Said surfaces that are inclined and blended with the lateral surface of the inhaling channel 3 are directed toward the second outlet 3b of the inhaling channel 3, so that the particles of the preparation in powder form, by striking said surfaces, are free to slide thereon, entrained by the stream of air generated by the suction of the user.

The second body 4 is provided with a through hole 10, which faces the opening of the reservoir 6. The hole 10 can be used conveniently in order to introduce the preparation in powder form in the reservoir 6 before the first body 2 is inserted in the receptacle 5 of the second body 4. Introduction of the preparation in the reservoir 6 and insertion of the first body 2 in the receptacle 5 can occur in a sterile environment, so that the inhaler, which contains a preset dose of preparation, can, in the same sterile environment, be enclosed in a sterile package and used as a single-use device.

The inhaler according to the present invention achieves important advantages.

First of all, it comprises substantially just two components, i.e., the first body 2 and the second body 4, the assembly of which is moreover extremely simple. Accordingly, the inhaler has a distinctly low cost and is practically free from risks of jamming or malfunction, being particularly advantageous for single-use application. Perfect suitability for single-use application is determined by the presence of the reservoir 6 and by its position with respect to the lateral outlet 3c of the inhaling channel 3: when the first body 2 is in the first position with respect to the second body 4, the dose of preparation in powder form contained inside the reservoir 6 is in fact perfectly sealed with respect to the outside, becoming available for inhaling only following the rotation of the first body 2 into the second position. Moreover, since the drug is inside the inhaling channel and inside the air stream drawn by the suction of the user, the capsule with the inhaler gives user assurance that the dose of preparation is taken in full since said dose is entrained effectively by the stream of suction air. By virtue of this characteristic, the inhaler can be kept in a substantially horizontal position during inhaling. In this position, the longitudinal axis of the inhaling channel is aligned with the mouth of the user, allowing the aspirated drug to reach directly the trachea without stopping on the internal parts of the mouth.

The disclosures in Italian Patent Application No. MO2004A000060 from which this application claims priority are incorporated herein by reference.

The invention claimed is:

1. An inhaler for dispensing preparations in powder form, comprising:
   a first body (2) including an inhaling channel (3) extending through and along a longitudinal axis (x) of said first body (2); and
   a second body (4) including a receptacle (5),
   wherein
   said first body (2) is inserted into said receptacle (5), said inhaling channel (3) of said first body (2) having a first outlet (3a) capable of and adapted to dispense preparation in powder form to a user's mouth, and arranged outside the receptacle (5), the inhaling channel (3) having a second outlet (3b) inside the receptacle (5) of the second body (4), said inhaling channel (3) has at least one lateral outlet (3c) inside the receptacle (5), facing perpendicular to the longitudinal axis (x) of the first body (2), said second body includes at least one reservoir (6) having an opening to said receptacle (5) and being capable of and adapted to contain a dose of preparation in powder form, said reservoir (6) projects perpendicular to the longitudinal axis (x) of the first body (2), said first body (2) is capable of rotating about its own longitudinal axis (x) with respect to the second body (4) between a first position, at which the lateral outlet (3c) of the inhaling channel (3) does not connect with the opening of the reservoir (6) so that said reservoir (6) is not connected to the inhaling channel (3), and a second position, in which the lateral outlet (3c) of the inhaling channel (3) connects the opening of the reservoir (6) so that said reservoir (6) is connected to the inhaling channel (3), and the second body (4) is provided with a through channel (7) having a second outlet (7b) arranged on the outer surface of one end of the second body (4).

2. The inhaler according to claim 1, wherein the first outlet (3a) and the second outlet (3b) are arranged approximately at right angles to the longitudinal (x) of the first body (2), the end at which the second outlet (3b) is arranged being in contact with an end wall (5b) of the receptacle (5) that is perpendicular to the longitudinal axis (x).

3. The inhaler according to claim 1, wherein the through channel (7) has a first outlet (7a) arranged at the bottom of an end wall (5b) of the receptacle (5), said first outlet (7a) of the through channel (7) being arranged in a position in which it faces the second outlet (3b) of the inhaling channel (3) at least at the second position of the first body (2).

4. The inhaler according to claim 1, wherein the inhaling channel (3) has at least one first protrusion (8), which protrudes transversely to the longitudinal axis (x) of the first body (2) from the lateral surface of the inhaling channel (3) toward the inside of said inhaling channel (3).

5. The inhaler according to claim 4, wherein the inhaling channel (3) has at least one second protrusion (9), which protrudes transversely to the longitudinal axis (x) of the first body (2) from the lateral surface of the inhaling channel (3) toward the inside of said inhaling channel (3), said second protrusion (9) being spaced with respect to the first protrusion (8) toward the longitudinal axis (x) of the first body (2) and being arranged opposite with respect to a central plane of the inhaling channel (3).

6. The inhaler according to claim 5, wherein said first and second protrusions (8, 9) have at least one surface that is inclined and blended with the lateral surface of the inhaling channel (3), said surfaces that are inclined and blended with the lateral surface of the inhaling channel (3) being directed toward the second outlet (3b) of the inhaling channel (3).

7. The inhaler according to claim 1, wherein the second body (4) is provided with a through hole (10), which faces the opening of the reservoir (6).

8. The inhaler according to claim 2, wherein the lateral outlet (3c) and the second outlet (3b) of the inhaling channel (3) form a single opening that lie between one end and a portion of the lateral surface of the first body (2).

9. The inhaler according to claim 3, wherein the inhaling channel (3) has at least one first protrusion (8), which protrudes transversely to the longitudinal axis (x) of the first body (2) from the lateral surface of the inhaling channel (3) toward the inside of said inhaling channel (3);

wherein the inhaling channel (3) has at least one second protrusion (9), which protrudes transversely to the longitudinal axis (x) of the first body (2) from the lateral surface of the inhaling channel (3) toward the inside of said inhaling channel (3), said second protrusion (9) being spaced with respect to the first protrusion (8) toward the longitudinal axis (x) of the first body (2) and being arranged opposite with respect to a central plane of the inhaling channel (3); and wherein the second body (4) is provided with a through hole (10), which faces the opening of the reservoir (6).

* * * * *